(12) United States Patent
Osier et al.

(10) Patent No.: US 8,434,485 B2
(45) Date of Patent: May 7, 2013

(54) RESPIRATORY MASK

(75) Inventors: Samuel W. Osier, Hemet, CA (US); Steven J. Duquette, Laguna Niguel, CA (US); Harold E. Miller, Upland, CA (US)

(73) Assignee: CareFusion 2200, Inc., San Diego, CA (US)

(*) Notice: Subject to any disclaimer, the term of this patent is extended or adjusted under 35 U.S.C. 154(b) by 1131 days.

(21) Appl. No.: 12/346,044

(22) Filed: Dec. 30, 2008

(65) Prior Publication Data

US 2010/0163049 A1 Jul. 1, 2010

(51) Int. Cl.
*A62B 18/08* (2006.01)

(52) U.S. Cl.
USPC .................................... 128/206.24

(58) Field of Classification Search ............. 128/205.25, 128/206.21, 206.24, 206.28, 207.11, 207.13, 128/202.27
See application file for complete search history.

(56) References Cited

U.S. PATENT DOCUMENTS

| | | |
|---|---|---|
| 812,706 A | 2/1906 | Warbasse |
| 853,439 A | 5/1907 | Clark |
| 858,439 A | 7/1907 | Cantwell |
| 1,155,608 A | 10/1915 | Nieschang |
| 1,176,886 A | 3/1916 | Ermold |
| 1,849,745 A | 3/1932 | Hoffman |
| 2,259,817 A | 10/1941 | Hawkins |
| 2,590,006 A | 3/1952 | Gordon |
| 3,388,705 A | 6/1968 | Grosshandler |
| 3,670,726 A | 6/1972 | Mahon et al. |
| 3,964,488 A | 6/1976 | Ring et al. |
| 4,018,221 A | 4/1977 | Rennie |
| 4,593,688 A | 6/1986 | Payton |
| 4,593,690 A | 6/1986 | Sheridan et al. |
| 4,641,647 A | 2/1987 | Behan |
| 4,732,147 A | 3/1988 | Fuller |
| 4,774,946 A | 10/1988 | Ackerman et al. |
| 4,852,564 A | 8/1989 | Sheridan et al. |
| 4,919,128 A | 4/1990 | Kopala et al. |
| 4,944,310 A | 7/1990 | Sullivan |
| 5,024,220 A | 6/1991 | Holmgreen et al. |
| 5,042,478 A | 8/1991 | Kopala et al. |
| 5,243,971 A | 9/1993 | Sullivan et al. |
| 5,269,296 A | 12/1993 | Landis |
| 5,477,852 A | 12/1995 | Landis et al. |
| 5,558,090 A | 9/1996 | James |

(Continued)

FOREIGN PATENT DOCUMENTS

| | | |
|---|---|---|
| DE | 29810846 U1 | 10/1998 |
| EP | 0549299 A2 | 6/1993 |

(Continued)

OTHER PUBLICATIONS

PCT Invitation to Pay Additional Fees mailed Jun. 1, 2010 (6 pages).

(Continued)

*Primary Examiner* — Glenn Richman
(74) *Attorney, Agent, or Firm* — McDermott Will & Emery LLP

(57) ABSTRACT

A respiratory mask includes a mask frame, a cushion and a retaining element. The retaining element is embedded within the cushion and is configured to secure the cushion to the mask frame. Forehead pads can be positioned in the mask frame and be adjustable independent of one another and with respect to the mask frame.

16 Claims, 5 Drawing Sheets

U.S. PATENT DOCUMENTS

| | | | |
|---|---|---|---|
| 5,687,715 | A | 11/1997 | Landis et al. |
| 6,012,455 | A | 1/2000 | Goldstein |
| 6,044,844 | A | 4/2000 | Kwok et al. |
| 6,112,746 | A | 9/2000 | Kwok et al. |
| 6,119,693 | A | 9/2000 | Kwok et al. |
| D439,326 | S | 3/2001 | Hecker et al. |
| 6,427,694 | B1 | 8/2002 | Hecker et al. |
| 6,463,931 | B1 | 10/2002 | Kwok et al. |
| 6,860,269 | B2 | 3/2005 | Kwok et al. |
| 7,007,696 | B2 | 3/2006 | Palkon et al. |
| 2002/0096173 | A1 | 7/2002 | Berthon-Jones et al. |
| 2006/0124131 | A1 | 6/2006 | Chandran et al. |
| 2008/0053446 | A1 | 3/2008 | Sleeper et al. |
| 2008/0276937 | A1 | 11/2008 | Davidson et al. |

FOREIGN PATENT DOCUMENTS

| | | | |
|---|---|---|---|
| EP | 1334742 | A2 | 8/2003 |
| WO | 8203548 | A1 | 10/1982 |
| WO | 9848878 | A2 | 11/1998 |
| WO | 9943375 | A1 | 9/1999 |
| WO | 9965554 | A1 | 12/1999 |
| WO | 0211804 | A2 | 2/2002 |
| WO | 03105921 | A2 | 12/2003 |
| WO | 2004022145 | A1 | 3/2004 |

OTHER PUBLICATIONS

Photograph of Weinmann mask, acquired prior to 1998.
Sullivan Mirage brochure, copyright 1997, ResMed Ltd.
Sullivan Mirage brochure, copyright 1998, ResMed Ltd.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, De Vilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schalldaempfer (medium), Part #WN23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc., Hans Rudolph Silicone Rubber Face Mask/8900.
Mask 1 Photographs, Respironics Inc., Reusable Full Mask (small) Part #452033 Lot #951108.
Mask 2 Photographs, Puritan-Bennett, Adam Curcuit, Shell Part #231700, Swivel Part #616329-00, Pillows (medium) Part #616324.
Mask 3 Photographs, De Vilbiss Healthcare Inc., Devilbiss Seal-Ring and CPAP Mask Kit (medium), Part #73510-669.
Mask 4 Photographs, Respironics Inc., Monarch Mini Mask with Pressure Port. Part #572004, Monarch Headgear, Part #572011.
"The ResMed Range of Mask Systems" product brochure, Nov. 1995, 4 pages.
Somnotron CPAP-Gerat WM 2300 instruction manual, Weinmann Hamburg, 11 pages, 1991.
9 Photographs of Weinmann mask, WM 23122, 1991.
PCT International Search Report and Written Opinion mailed Oct. 4, 2010 (22 pgs.).

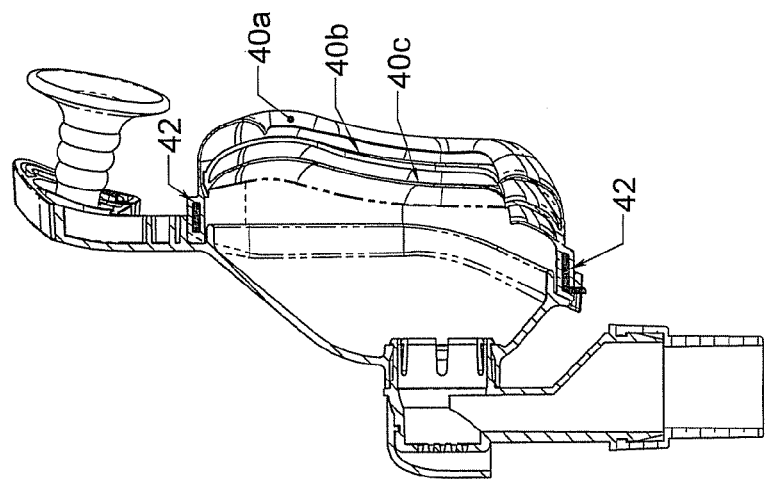
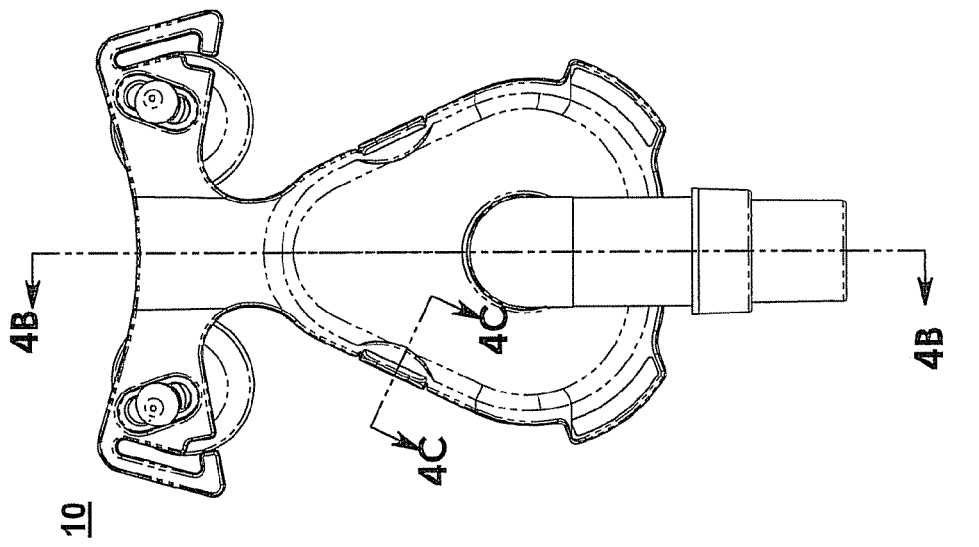
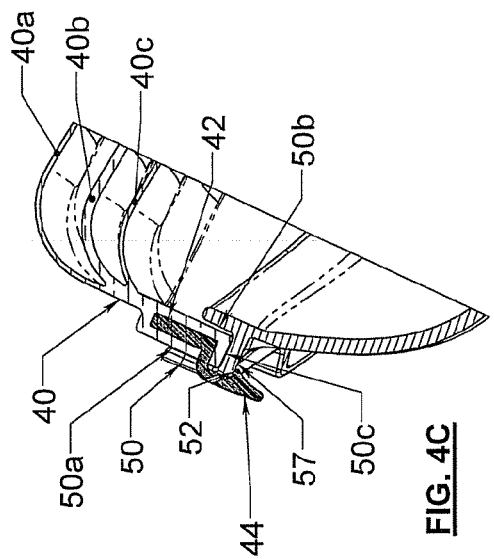
FIG. 4B
FIG. 4A
FIG. 4C

RESPIRATORY MASK

BACKGROUND

The present disclosure relates to respiratory masks. Respiratory masks are used in several different situations for treatment of respiratory disorders, for example obstructive sleep apnea. During treatment, a flow of breathable gas is provided to a patient through the mask. Current mask designs generally include a mask frame or body coupleable to a conduit that delivers the breathable gas flow. A cushion is coupled to the mask frame and presses against the patient to provide comfort and cover the nose and/or mouth of the patient. Additionally, a forehead pad can be provided for cushioning the mask against the forehead of the patient. Straps are provided to secure the mask to the patient's head.

One concern in mask design is assembly of mask components. In some instances, masks utilize a retaining ring to secure the cushion of the mask to the mask frame. One method of securing the cushion to the mask frame includes ultrasonically welding the retaining ring to the mask frame so as to permanently secure the cushion to the mask frame. The ultrasonic welding process requires tools to assemble the mask, which can add to the cost of the mask. Furthermore, while this method is effective in securing the cushion to the mask frame, there are additional disadvantages in having the cushion permanently secured to the mask frame. For example, some insurance companies only reimburse a patient for cushion replacement on a regular basis. Permanent assembly of the cushion to the mask frame prevents the patient from only replacing the cushion. Due to the lack of reimbursement, the patient, in some instances, will defer replacement of the mask or have to pay for a new mask out-of-pocket. Furthermore, the mask can be difficult to clean when the cushion and mask frame are assembled, leading to potentially unsanitary conditions.

In another method of securing the cushion to the mask, a separate retaining ring secures the cushion around its edges by utilizing a tongue and groove connection on either the outside or inside of the cushion. In yet another method, the cushion can be secured to the mask frame by sandwiching the cushion edge between the mask frame and the retaining ring. In any event, by utilizing a retaining ring that is separate from the cushion, securing the cushion to the mask frame can be cumbersome and time consuming. For example, it may be difficult to properly align the cushion and the retaining ring so as to properly secure the cushion to the mask frame.

Another concern in mask design is comfort to the patient. Current masks can be uncomfortable and unable to accommodate different shapes and/or sizes of heads. For example, forehead pads can be stiff and thus not conform to various foreheads. In other masks, forehead pads can be adjustable, but many masks are difficult to conform to different shapes and/or sizes of heads and thus not desirable. Additionally, forehead pads may be formed of a material that retains water. As a result, water may be retained in the forehead pad after cleaning. Further still, perspiration from the patient can be retained in the forehead pad. Both of these situations can lead to unsanitary conditions.

SUMMARY

One aspect of the present disclosure relates to a respiratory mask for use in a respiratory therapy system. The mask includes a mask frame, a cushion and a retaining element. The retaining element is embedded within the cushion and adapted to secure the cushion to the mask frame. In one particular embodiment, tabs extend from the retaining element through the cushion and are used to secure the retaining element to the mask frame. A groove can be provided on the mask frame to receive the cushion and embedded retaining element.

Another aspect relates to forehead pads coupled to the mask frame for selective adjustment of the mask frame relative to a head of the patient. The forehead pads can be adjusted independent of one another so the mask can comfortably fit a number of different patients as well as accommodate movement of a patient. In one embodiment, the forehead pads can define a bellows region that can be positioned in a grooved slot of the mask frame.

BRIEF DESCRIPTION OF THE DRAWINGS

FIG. 4A is a front view of the mask assembly of FIG. 1.
FIG. 4B is a sectional view along line 4B-4B of FIG. 4A.
FIG. 4C is a sectional view along line 4C-4C of FIG. 4A.

DETAILED DESCRIPTION

Figure 1:
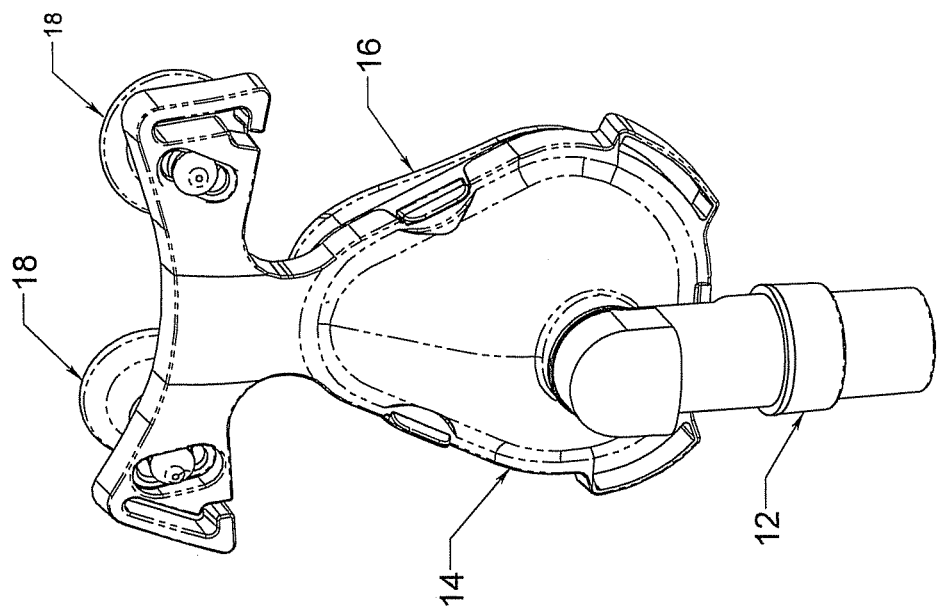
FIG. 1 is an isometric view of a mask assembly.

FIG. 1 is an isometric view of a mask or mask assembly 10 for use in a respiratory therapy system such as a Continuous Positive Airway Pressure (CPAP) system. In a respiratory therapy system, gas flow is provided to a patient through mask assembly 10, which can be secured to a head of the patient. Mask assembly 10 includes a gas supply conduit connector 12, a mask frame or body 14, a cushion assembly 16 and first and second forehead pads 18. Connector 12 is coupleable to a gas supply for delivery of gas to the mask frame 14. Straps (not shown) are coupled to the mask frame 14 in order to secure mask assembly 10 to the head of the patient.

Cushion assembly 16 is secured to mask frame 14 and configured to press against a face of the patient and cover a nose of the patient. In other embodiments, the mask frame can further cover the mouth of the patient. In any event, the cushion assembly 16 is designed to create a relatively air tight seal with the face of the patient such that gas flow is delivered to a patient airway (e.g. mouth, sinus). Forehead pads 18 press against a forehead of the patient and can be adjustably positioned with respect to the mask frame 14. In one embodiment, adjustments to the forehead pads 18 are made automatically based on movement of the patient. In another embodiment, manual adjustments to the forehead pads are made in order to adjust to a specific size and/or shape of the patient's head.

Figure 2:
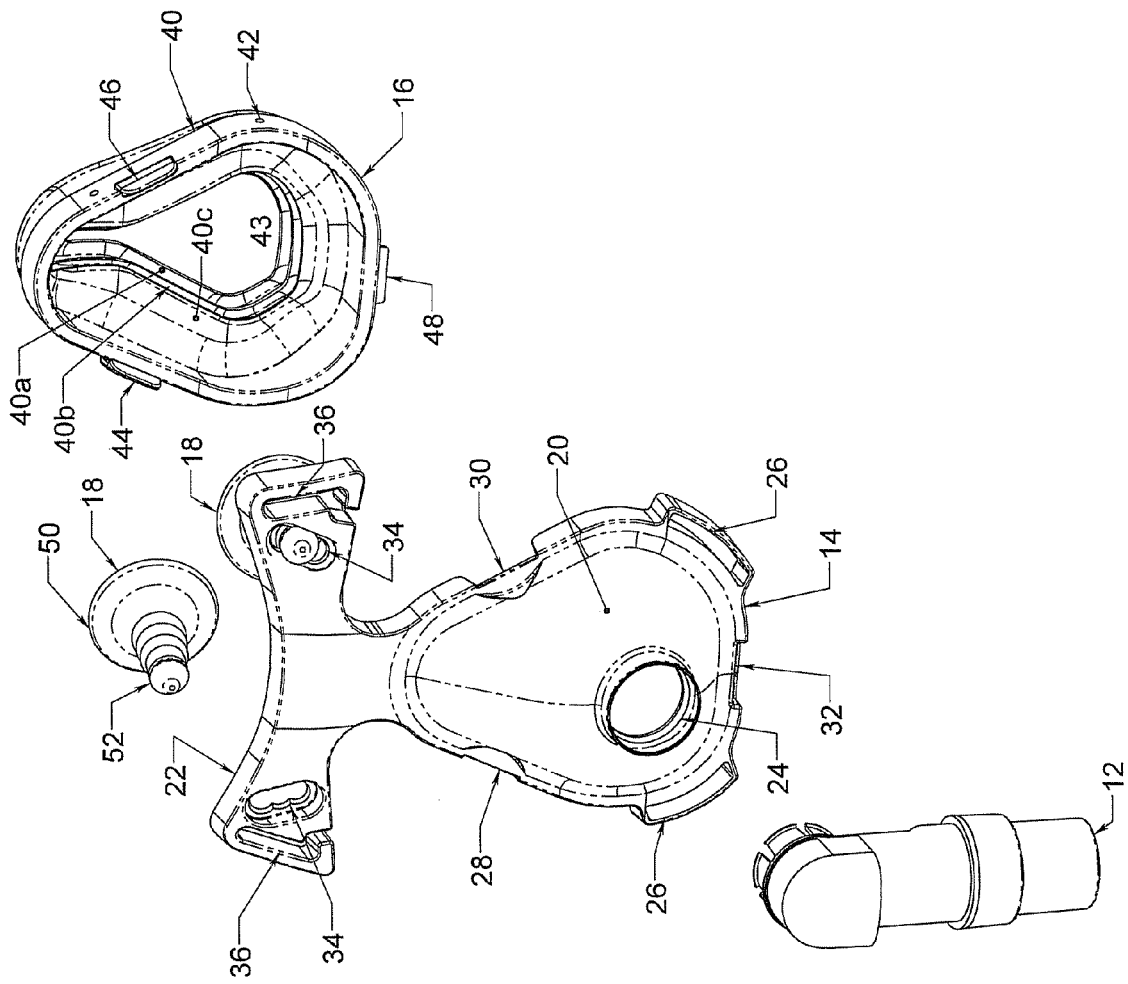
FIG. 2 is an exploded view of the mask assembly of FIG. 1.

With further reference to FIG. 2, mask frame 14 includes a mask shell 20 and a bridge portion 22. Mask shell 20 defines an opening 24 for receiving the gas conduit connector 12. During operation, gas flows from conduit connector 12 and through opening 24 to the patient. Mask shell 20 also defines first and second strap receiving portions 26 and tab receiving portions 28, 30 and 32. A strap (not shown) is provided in the strap receiving portions 26 to secure a lower portion of the mask frame 14 to the patient's head. Tab receiving portions 28, 30 and 32 receive corresponding tabs of the cushion assembly 16 such that the cushion assembly 16 can be releasably secured to the mask frame 14. Furthermore, assembly of the cushion assembly 16 to the mask frame 14 can be performed quickly and without the need for specialized assembly tools.

Bridge portion 22 is generally T-shaped and defines first and second slots 34 for receiving the first and second forehead pads 18. Together, the first and second forehead pads 18 cooperate with the first and second slots 34 to selectively adjust mask frame 14 with respect to the patient's head. In particular, forehead pads 18 can be selectively adjusted vertically (i.e., up and down with respect to the slots 34) as well as horizontally (i.e., in and out with respect to the slots 34). To this end, both of the forehead pads 18 and both slots 34 are grooved to facilitate selective position adjustment. Additionally, the forehead pads 18 can move with respect to mask frame 14 independent of one another, which can lead to a more comfortable fit. Additionally, bridge portion 22 includes first and second strap receiving portions 36 adapted to receive a strap (not shown) for securing mask assembly 10, in particular an upper portion thereof, to the forehead of the patient.

Cushion assembly 16 is formed of a cushion 40 and a retaining element or ring 42. In the embodiment illustrated, cushion 40 includes three overlapping layers 40a, 40b and 40c of material to provide support and sealing around the patient's nose. In particular, layer 40a overlaps layers 40b and 40c, and wherein layer 40b overlaps layer 40c. Cushion 40 also forms an opening 43 in fluid communication with opening 24 on mask shell 20 so as to direct gas flow from the gas conduit connector 12 to the patient. Retaining element 42 is embedded within cushion 40 and is adapted to secure cushion 40 to mask shell 20. By embedding retaining element 42 within cushion 40, cushion assembly 16 can easily be assembled to the mask frame 14 without the need to align cushion 40 with retaining element 42 to create a proper seal between cushion assembly 16 and mask frame 14. In order to secure cushion 42 to mask shell 20, retaining element 42 includes tabs 44, 46 and 48 that are configured to be placed in tab receiving portions 28, 30 and 32 of mask shell 20, respectively.

In one embodiment, retaining element 42 is embedded within cushion 40 by an over molding process wherein tabs 44, 46 and 48 extend through cushion 40 and remain exteriorly exposed while the remaining portion of retaining element is embedded within cushion 40. Stated another way, the cushion 40 completely surrounds a circumference of the retaining element 42. With the exception of the tabs 44, 46 and 48, only the cushion material of the cushion assembly 16 is exteriorly exposed. Cushion 40 can be made of an elastomeric material such as silicone, a thermoplastic elastomer, etc. Retaining element 42 provides structural integrity to cushion 40 and engages mask frame 14 to secure cushion 40 to mask frame 14. To this end, retaining element 42 can be formed of a material that is more rigid than cushion 40, for example a rigid plastic material such as polycarbonate, polypropylene, etc.

Figure 3:
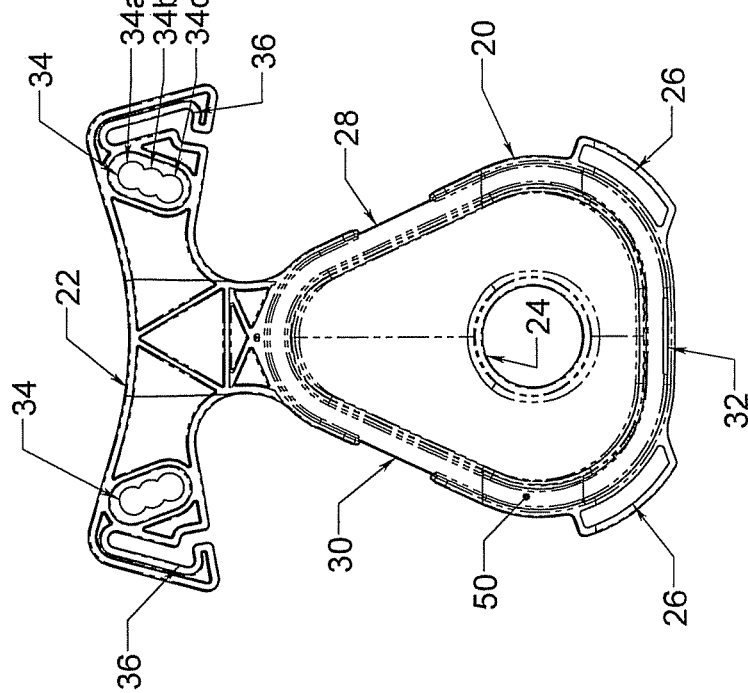
FIG. 3 is a rear isometric view of a mask frame.

With further reference to FIG. 3, a rear view of mask frame 14 is illustrated. Mask shell 20 includes an annular groove 50 shaped to receive cushion assembly 16. In particular, annular groove 50 is generally U-shaped along a cross section and has a thickness to accommodate cushion 40 and retaining element 42. During assembly of mask assembly 10, tab 48 is inserted into tab receiving portion 32 and cushion assembly 16 is inserted into annular groove 50. In the embodiment illustrated, tab 48 is a projection adapted for insertion into tab receiving portion 32, which is an aperture in mask shell 20. Next, tabs 44 and 46 of retaining element 42 are pressed against tab receiving portions 28 and 30, respectively, locking into place against mask shell 20. Both of tabs 44 and 46 are hook shaped to engage respective tab receiving portions 28 and 30, which form recess portions in groove 50. In particular, the hook portions engage a front side of mask frame 14 (i.e., closer to opening 24 and on a side opposite annular groove 50).

FIG. 4A is a front view of mask assembly 10, illustrating section line 4B-4B for FIG. 4B and section line 4C-4C for FIG. 4C. Together, FIGS. 4A-4C illustrate connection between mask frame 14 and cushion assembly 16. FIG. 4C is a close-up, sectional view of engagement between tab 44 of retaining element 42 and tab receiving portion 28 of mask shell 20. As illustrated, retaining element 42 is embedded within cushion 40, such that cushion 40 completely surrounds the circumference of retaining element 42 on all sides. Together, cushion 40 and retaining element 42 are disposed within annular groove 50. Illustratively, the U-shaped annular groove 50 includes three sides 50a, 50b and 50c. Cushion 40 surrounds retaining element 42 such that cushion 40 is exteriorly exposed to all three sides (50a, 50b and 50c) of annular groove 50. In one embodiment, the resilient nature of cushion 40 can allow cushion assembly 16 to fit tightly within annular groove 50, as cushion 40 slightly compresses to fit into groove 50 and contacts at least sides 50a and 50b of groove 50 and, in one embodiment, also contacts side 50c. Tab 44 of retaining element 42 extends through cushion 40 and around tab receiving portion 28. Tab 44 can be resilient and shaped so as to deflect around tab receiving portion 28. A hook portion 52 of tab 44 snaps against tab receiving portion 28 to secure cushion assembly 16 to mask shell 20 once hook 52 is against a front side 54 of tab receiving portion 28.

Figure 5B:
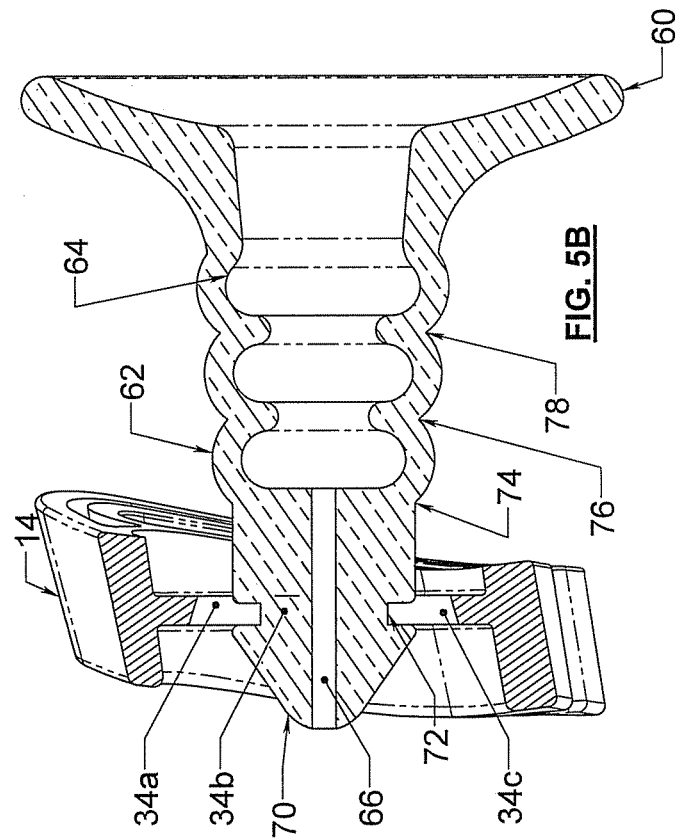
FIG. 5B is a sectional view along line 5B-5B of FIG. 5A.
Figure 5A:
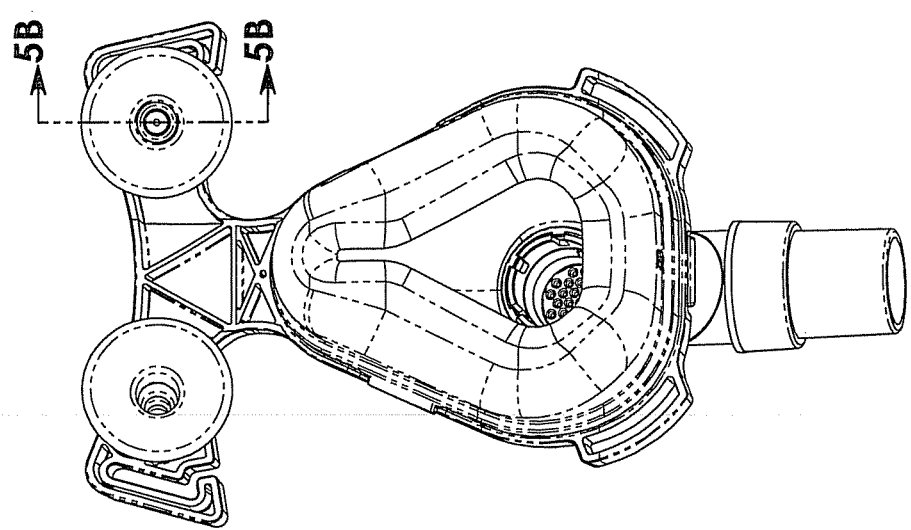
FIG. 5A is a rear view of the mask assembly of FIG. 1

FIG. 5A is a rear view of mask assembly 10, illustrating section line 5B-5B for FIG. 5B. FIG. 5B is a sectional view of one of the forehead pads 18 that includes a pad region 60 and a tapered bellows region 62. In one embodiment, forehead pad 18 can be made of a rubber material such as silicone, a thermoplastic elastomer, etc. As illustrated, pad region 60 is concave shaped and presses against the forehead of the patient. Bellows region 62 extends from the pad region 60, defining an interior cavity 64 and an air channel 66, which terminates at a tip end 70. Interior cavity 64 allows bellows region 62 to be flexible such that pad region 60 can maintain constant contact with the patient's forehead. Air channel 66 prevents forehead pad 18 from sticking to the patient's forehead as well as promoting drainage of fluids from cleaning and/or perspiration.

Tip end 70 is adapted for insertion into one of the slots 34 on mask frame 14. After insertion of tip end 70 into slot 34, bellows region 62 can be selectively adjustable to discrete positions within slot 34 as a function of grooves 72, 74, 76 and 78. For example, if it is desired to have mask frame 14 further away from the patient's face, forehead pad 18 can be adjusted such that groove 72 engages slot 34 (as illustrated in FIG. 5B). If it is desired to have mask frame 14 closer to the patient's face, forehead pad 18 can be adjusted such that groove 78 engages slot 34. Additionally, the forehead pad 18 can move to different vertical positions within slot 34 and thus with respect to mask frame 14. Slot 34 includes a plurality of grooves, in particular three grooves, which are illustrated in FIG. 3 as well as in section in FIG. 5B, namely a top groove 34a, a middle groove 34b and a bottom groove 34c. As illustrated in FIG. 5B, forehead pad 18 is positioned in middle groove 34b. If it is desired for mask frame 14 to sit lower with respect to the patient's head, forehead pad 18 can be adjusted to be positioned in the top groove 34a of slot 34. If it is desired for mask frame 14 to sit higher with respect to the patient's head, the forehead pad 18 can be adjusted to be positioned in the lower groove 34c of slot 34. Due to the resilient nature of forehead pad 18, a position of forehead pad 18 in slot 34 can adjust automatically, for example based on patient movement.

Although the present disclosure has been described with reference to preferred embodiments, workers skilled in the art will recognize that changes can be made in form and detail without departing from the spirit and scope of the present disclosure.

What is claimed is:

1. A respiratory mask, comprising:
a mask frame defining a groove;
a cushion formed of a first material; and
a retaining element formed of a second material that is more rigid than the first material, embedded within the entire perimeter of said cushion and adapted to be releasably secured to the mask frame, wherein the cushion and retaining element are disposed within the groove such that the cushion is exteriorly exposed to the groove.

2. The respiratory mask of claim 1 wherein the retaining element includes a plurality of tabs positioned within corresponding tab receiving portions of the mask frame.

3. The respiratory mask of claim 2 wherein the plurality of tabs each extend through the cushion.

4. The respiratory mask of claim 1 wherein the mask frame further includes a bridge that includes first and second slots that engage first and second foreheads pads, each of the first and second forehead pads adapted to be positioned with respect to the mask frame independent of the other forehead pad.

5. The respiratory mask of claim 4 wherein the first and second forehead pads each include a bellows section defining grooves for selective positioning in the first and second slots.

6. The respiratory mask of claim 5 wherein each bellows region defines an air channel at a tip end of the bellows region.

7. The respiratory mask of claim 1 wherein the cushion includes a plurality of overlapping layers.

8. A method of assembling a respiratory mask, comprising:
providing a mask frame;
forming a cushion assembly including a cushion formed of a first material and a retaining element formed of a second material embedded within the entire perimeter of said cushion, the second material being more rigid than the first material;
providing an annular, u-shaped groove in the mask frame; and
positioning the cushion assembly in the groove such that the cushion contacts the groove and the retaining element is disposed within the groove; and
securing the cushion assembly to the mask frame using the retaining element.

9. The method of claim 8 and further comprising:
providing a tab receiving portion on the mask frame having a first side and a second side;
providing a tab extending from the retaining element through the cushion;
positioning the tab in the tab receiving portion such that the tab contacts the first side of the tab receiving portion and the cushion contacts the second side of the tab receiving portion.

10. The method of claim 8 and further comprising:
providing first and second grooved slots in the mask frame; and
providing first and second forehead pads in the first and second slots, respectively, wherein the first and second pads are adjustable with respect to each other and the mask frame.

11. The method of claim 10 wherein the first and second forehead pads each include a bellows region defining grooves for selective positioning in the first and second slots.

12. The method of claim 11 and further comprising:
forming an air channel in a tip end of each bellows region.

13. The method of claim 8 and further comprising:
forming a plurality of overlapping layers in the cushion.

14. A respiratory mask for use in delivering gas flow to a patient received from a respiratory therapy system, comprising:
a mask frame defining a mask shell forming an opening to receive the gas flow and a bridge portion extending from the mask shell and defining first and second slots;
a cushion assembly including a cushion and a retaining element embedded in the cushion, the retaining element including tabs to secure the cushion to the mask shell, said mask frame coupled to the entire perimeter of said cushion; and
first and second forehead pads positioned in the first and second slots of the bridge portion, the first and second forehead pads being independently adjustable with respect to one another and with respect to the mask frame in both horizontal and vertical directions.

15. The respiratory mask of claim 14 wherein the first and second forehead pads each include a pad region and a tapered bellows region, the tapered bellows region defining an air channel at a tip end of the bellows region.

16. The respiratory mask of claim 14 wherein the mask frame defines an annular groove and a plurality of tab receiving portions and wherein the cushion assembly is inserted into the groove such that the tabs engage the tab receiving portions.

* * * * *